United States Patent
Greening et al.

[19]

[11] Patent Number: 6,151,164
[45] Date of Patent: *Nov. 21, 2000

[54] STEREOSCOPIC VIEWING SYSTEM USING A TWO DIMENSIONAL LENS SYSTEM

[75] Inventors: Anthony B. Greening, North Vancouver; Thomas N. Mitchell, Richmond, both of Canada

[73] Assignee: International Telepresence (Canada) Inc., Canada

[ * ] Notice: This patent is subject to a terminal disclaimer.

[21] Appl. No.: 09/166,618

[22] Filed: Oct. 5, 1998

Related U.S. Application Data

[63] Continuation of application No. 08/659,379, Jun. 6, 1996, Pat. No. 5,828,487, which is a continuation-in-part of application No. 08/227,556, Apr. 14, 1994, abandoned.

[51] Int. Cl.[7] .............................. G02B 27/22; A61B 1/04; H04N 13/02
[52] U.S. Cl. .......................... 359/466; 359/464; 359/462; 348/45; 348/49; 348/56; 600/11
[58] Field of Search .................... 359/462, 464, 359/466; 348/45, 49, 55, 56; 352/62, 63, 57; 600/111

[56] References Cited

U.S. PATENT DOCUMENTS

| | | | |
|---|---|---|---|
| 2,066,680 | 1/1937 | Gieskieng et al. | 250/201 |
| 2,255,631 | 9/1941 | Schulman | 88/39 |
| 2,967,905 | 1/1961 | Hirsch | 178/6.5 |
| 3,251,933 | 5/1966 | Beste | 178/6.5 |
| 3,438,689 | 4/1969 | Wehr | 350/42 |
| 3,536,921 | 10/1970 | Caulfield | 250/199 |
| 3,712,199 | 1/1973 | Songer | 95/18 R |
| 3,784,291 | 1/1974 | Hirata et al. | 352/169 |
| 4,021,846 | 5/1977 | Roese | 358/92 |
| 4,059,336 | 11/1977 | Hopkins | 350/55 |
| 4,145,713 | 3/1979 | White | 358/92 |
| 4,174,884 | 11/1979 | Weissler | 350/138 |
| 4,196,966 | 4/1980 | Malis | 350/145 |
| 4,303,316 | 12/1981 | McElveen | 352/57 |

(List continued on next page.)

FOREIGN PATENT DOCUMENTS

| | | |
|---|---|---|
| 687.68.659 | 2/1968 | Monaco . |
| 1075448 | 2/1984 | Russian Federation . |
| 1538282 | 1/1990 | Russian Federation . |
| 732472 | 6/1955 | United Kingdom . |
| 2256992 | 12/1992 | United Kingdom . |
| WO 95/14952 | 6/1995 | WIPO . |
| WO 95/28662 | 10/1995 | WIPO . |

OTHER PUBLICATIONS

Patent Abstracts of Japan, vol. 12, No. 331 (P–755) Sep. 7, 1988 & JP,A,63 094 216 (Toshiba).

(List continued on next page.)

*Primary Examiner*—Audrey Chang
*Attorney, Agent, or Firm*—Townsend and Townsend and Crew LLP

[57] ABSTRACT

A stereoscopic viewing system provides stereoscopic viewing using a two dimensional lens system and without having to have two cameras. The system may be used over a wide range of frequencies, in fact all frequencies that can be used for producing or reproducing an image. The viewing system has an opaque leaf positioned between the two dimensional lens system and a camera in a single image path, the opaque leaf is movable laterally in the single image path from a left position to a right position to provide a left image perspective and a right image perspective of the image path to the camera. A switching device moves the opaque leaf between the two positions and retains the leaf stationary in each position for a sufficient time for the camera to view each image perspective. A synchronizing system alternates the left image perspective and the right image perspective from the imaging system with a stereoscopic viewing device so that a viewer sees only the left image perspective with one eye and only the right image perspective with the other eye.

48 Claims, 2 Drawing Sheets

U.S. PATENT DOCUMENTS

| | | | |
|---|---|---|---|
| 4,392,710 | 7/1983 | Rogers | 350/505 |
| 4,461,541 | 7/1984 | Duthie | 350/132 |
| 4,480,893 | 11/1984 | Fantone | 350/132 |
| 4,523,226 | 6/1985 | Lipton et al. | 358/88 |
| 4,559,556 | 12/1985 | Wilkins | 358/88 |
| 4,562,463 | 12/1985 | Lipton | 358/88 |
| 4,568,160 | 2/1986 | Krueger | 352/86 |
| 4,582,393 | 4/1986 | Shieman | 350/132 |
| 4,601,552 | 7/1986 | Jessmore | 350/551 |
| 4,634,241 | 1/1987 | Kohayakawa et al. | 350/516 |
| 4,651,201 | 3/1987 | Schoolman | 358/98 |
| 4,654,699 | 3/1987 | Medina | 358/88 |
| 4,695,130 | 9/1987 | Medina et al. | 350/132 |
| 4,709,263 | 11/1987 | Brumage | 358/88 |
| 4,714,319 | 12/1987 | Zeevi et al. | 350/144 |
| 4,740,836 | 4/1988 | Craig | 358/92 |
| 4,761,066 | 8/1988 | Carter | 350/510 |
| 4,763,968 | 8/1988 | Minami et al. | 350/516 |
| 4,842,395 | 6/1989 | Sato et al. | 350/519 |
| 4,844,583 | 7/1989 | Lo | 350/132 |
| 4,853,764 | 8/1989 | Sutter | 358/3 |
| 4,871,233 | 10/1989 | Sheiman | 350/286 |
| 4,907,860 | 3/1990 | Noble | 350/334 |
| 4,924,853 | 5/1990 | Jones et al. | 128/6 |
| 4,979,033 | 12/1990 | Stephens | 358/92 |
| 5,002,376 | 3/1991 | Hoppl et al. | 350/516 |
| 5,034,809 | 7/1991 | Katoh | 358/88 |
| 5,059,009 | 10/1991 | McKinley | 359/435 |
| 5,097,359 | 3/1992 | McKinley | 359/435 |
| 5,117,296 | 5/1992 | Hoebing | 359/21 |
| 5,122,650 | 6/1992 | McKinley | 250/208.1 |
| 5,132,838 | 7/1992 | Ohshita | 359/432 |
| 5,144,480 | 9/1992 | Ohshita | 359/432 |
| 5,157,550 | 10/1992 | Tsuchida et al. | 359/686 |
| 5,173,806 | 12/1992 | Ogata | 359/683 |
| 5,222,477 | 6/1993 | Lia | 348/45 |
| 5,260,773 | 11/1993 | Dischert | 358/3 |
| 5,471,237 | 11/1995 | Shipp | 348/46 |
| 5,502,480 | 3/1996 | Kuga et al. | 348/46 |
| 5,510,832 | 4/1996 | Garcia | 348/56 |
| 5,541,641 | 7/1996 | Shimada | 348/58 |
| 5,588,948 | 12/1996 | Takahashi et al. | 600/111 |
| 5,616,912 | 4/1997 | Robinson et al. | 250/201.1 |
| 5,828,487 | 10/1998 | Greening et al. | 359/466 |

OTHER PUBLICATIONS

Patent Abstracts of Japan, vol. 10, No. 254 (P–492) Aug. 30, 1986 & JP,A,61 080 221 (Toshiba).

3–D Imaging For Minimally Invasive Surgery Gets MD's Attention—Health Technology Trends—Jun. 1993 (pp. 4,5).

The Future: Telepresence and Other Developments—Nagy, Robertson & Mitchell—Minimally Invasive Surgery in Gastrointestinal Cancer—Published by Chruchill Livingstone 1993 (pp. 171–181).

Three–Dimensional Endoscopic Imaging For Minimal Access Surgery—Mitchell et al—J.R. Coll. Surg. Edinb, 38 Oct. 1993 (pp. 285–292).

New Technologies in Laparoscopic Surgery—Nagy et al, B.C. Medical Journal, vol. 36, No. 3, Mar. 1994 (pp. 179–183).

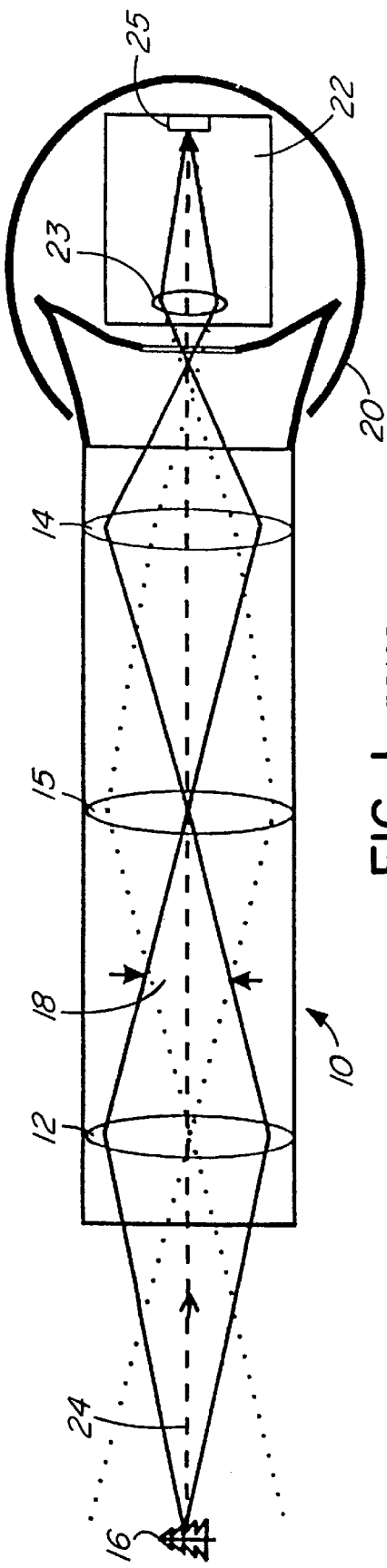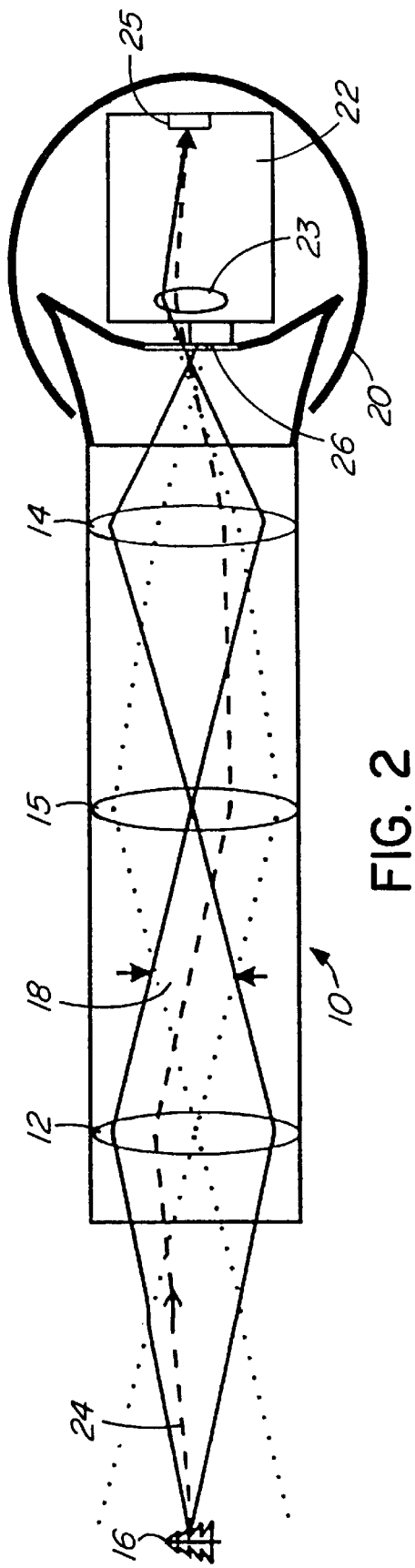

STEREOSCOPIC VIEWING SYSTEM USING A TWO DIMENSIONAL LENS SYSTEM

CROSS REFERENCE TO RELATED APPLICATIONS

This application is a continuation of U.S. patent application Ser. No. 08/659,379, filed Jun. 6, 1996, now U.S. Pat. No. 5,828,487 which in turn was a continuation-in-part of U.S. patent application Ser. No. 08/227,556, filed Apr. 14, 1994 now abandoned. U.S. patent application Ser. No. 08/659,379 and U.S. patent application Ser. No. 08/227,556 are incorporated herein in their entireties by reference.

TECHNICAL FIELD

The present invention relates to stereoscopic viewing of an image from a single lens imaging system such as a camera using a two dimensional lens system. More specifically, the present invention relates to a high speed switching device for producing stereoscopic images from a single image path.

BACKGROUND ART

Simple imaging systems used today are generally two dimensional. A camera has a single image path, or optical path and produces a two dimensional image. The term "camera" used throughout the specification means any type of single lens imaging system including a single imaging sensor which can produce or reproduce a picture of an object. Such cameras can operate in a wide frequency range extending from sonic frequencies to radio frequencies. Examples of such imaging systems include, but are not limited to, video cameras, film cameras, ultrasound systems and radio antennas.

Stereoscopic optical systems that produce three dimensional views are known. A majority of these systems include two separate cameras that provide separate side by side images and a method of blanking out alternate images from a left and right camera so the viewer sees the alternate images with a left eye followed by a right eye. These systems include active eyewear wherein shuttering occurs at the eyewear itself for viewing a monitor, or passive eyewear where the shuttering occurs at the monitor. In the case of video images, the monitor is frequently a standard 120 Hz monitor, therefore the emitter signals are synchronized to shutter alternate left and right lenses of the eyewear quickly at 120 Hz, the same speed as the monitor.

One use to which three dimensional imaging is now being used is minimal access surgery. In the known systems today dual lenses are provided in an endoscope with left and right cameras to provide left and right images for viewing. A description of existing systems are disclosed in a publication entitled "Three Dimensional Endoscopic Imaging for Minimal Access Surgery" by Mitchell et al, published October 1993, J. R. Coll. Surg. Edinb.

In two dimensional optical lens systems the rays from an object pass through entry lenses and are limited either by the edges of the lenses or an aperture stop within the lens system. This limitation of the rays is called the entry stop or entry aperture and defines the size of what is referred to as the entry pupil. The location of the entry pupil may be in front of the entry aperture or behind it. The entry pupil limits the angular aperture of the cone of rays that traverses the lens system. The exit pupil is the image of the entry aperture formed by all the parts of the lens system including the exit lenses that come after the entry aperture. The entry pupil and the exit pupil occupy conjugate positions, i.e., are coupled or twinned, with regards to the complete lens system. The principal ray from any object point is the one which passes through the center of the entry pupil.

If smaller aperture stops are placed within the lens system after the entry pupil, the complete cone of rays from the entry lens may not pass through the smaller stops. This effect, known as vignetting (i.e., partial occlusion), reduces the illumination of the image but does not change the angle of view passing through the entry pupil. This description of optical lens is disclosed by L. C. Martin in Geometrical Optics, published 1956 by Philosophical Library, Inc. (pages 71,72).

When a camera is coupled to the exit pupil, the rays defining the exit pupil are focused by the camera focusing lens to form an image on the light sensitive element in the camera. This is known as a two dimensional system, which has a single image path and applies to all types of two dimensional scopes.

In order to produce three dimensional or stereoscopic viewing, attempts have been made to place a shutter over half the entry aperture of the entry pupil and move the shutter from side to side. An example of such a system is disclosed by Lia in U.S. Pat. No. 5,222,477 which shows an endoscope, and by McElveen in U.S. Pat. No. 4,303,316 which relates to a process for recording visual scenes for reproduction in stereopsis. Krueger in U.S. Pat. No. 4,568,160 also shows inserting a refracting member between lenses. All of these systems shift the principal ray from the center of the entry pupil to one side. Thus, different perspectives, i.e., a left perspective and a right perspective, are produced which can provide stereoscopic viewing. The resulting image loses one F stop of light as the aperture stop of the entry pupil only has half the original area.

By placing a shutter in the lens system, or between the lens system and the object, it is generally required to design a special lens system for this purpose. As shown by Lia a special endoscope has to be constructed with the shutter at the external end of the scope.

Other methods of three dimensional viewing do not use a single image system. Various combinations of additional prisms, mirrors, refracting lenses have been positioned either in the entry pupil or the exit pupil. In all these cases two focusing lenses are needed instead of one as there are two separate sets of image rays or image paths that create two separate images.

Other types of stereoscopic optical systems are disclosed in U.S. Pat. No. 4,761,066 to Carter which utilizes a beam splitter. With regard to the viewers, an example of a liquid crystal stereoscopic viewer is disclosed by Roese in U.S. Pat. No. 4,021,846. The concept of utilizing a passive eyewear includes lenses with colored filters therein. Such a system is disclosed in U.S. Pat. No. 3,712,199 to Songer.

DISCLOSURE OF INVENTION

The present invention avoids the necessity of requiring two separate imaging systems and needs only a single image path between an image and a camera. This permits utilizing existing two dimensional lens systems such as endoscopes, boreoscopes, microscopes, telescopes and the like, including lens systems with offsets, mirrors and prisms. In all cases, only a single image path is required. It also permits use of video and film cameras with common optical lenses and other energy focusing devices to be incorporated. In the case of a conventional motion picture film camera or video camera, a fixed focal length lens or a variable focal lens may be incorporated in the present system which provides stereoscopic viewing.

Whereas the existing stereoscopic optical systems that use a single image path all require a special lens system that has a shutter or other mechanism in the lens system or else a position a shutter prism or the like between the object and the lens system, it has now been found that a two dimensional lens scope such as an endoscope, boreoscope, telescope or microscope can be adapted for stereoscopic viewing by placing a switching mechanism between the scope and the camera. This system allows use of existing scopes without having a switching device positioned between the scope and the object. Furthermore, a special system with two image paths is not required. The single image path lens system does not reduce the area of the entry pupil thus there is no reduction or limiting of the rays from the image entering the lens system.

A switching device is positioned between a two dimensional lens system and a camera. The switching device has an opaque leaf which is moved laterally at high speed in the image path from a left position to a right position to provide a left image perspective and a right image perspective. The left image perspective and right image perspective provide the stereoscopic viewing and a synchronizer is provided to synchronize with, for example, a vertical retrace in a video system, or a film gate mechanism for advancing a frame exposure in a film camera. The synchronizer provides a signal to the stereoscopic viewing system such that the left image perspective is visible to one eye, generally the left eye, and the right image perspective is visible to the other eye of a viewer. Thus, a three dimensional or stereoscopic image is achieved. Because the two perspectives see the object, there is no need to refocus or change the optics between perspectives. The object is seen from both perspectives.

In the case of utilizing a video camera, a signal from the camera indicating the frame exposure advancing cycle is used to synchronize the stereoscopic viewing system. The signal from a video camera may be transmitted by telecommunications to different viewers. Alternatively, the signal may be recorded on a VCR, compact disc, or other similar recording means for future viewing and, again, the indication of frame change from the VCR or projector in the case of a film, may be used to synchronize the stereoscopic viewing arrangement to blank out alternately a left lens and a right lens of the eyewear. The system may also be used for transmission signals, either through cable, satellite or radio media. The receiving viewer must have a stereoscopic viewing arrangement that is synchronized with the received transmission signals.

The present invention provides a stereoscopic viewing system for viewing an object in a single image path with a camera comprising: a two dimensional lens system on the single image path, a switching device having an opaque leaf positioned between the two dimensional lens system and the camera, the opaque leaf movable in the single image path from a left position to a right position, to provide a left image perspective and a right image perspective of the image path to the camera, the left image perspective and the right image perspective required for stereoscopic viewing; means for moving the opaque leaf between the left position and the right position, and retain the opaque leaf stationary in each position for a sufficient time for the camera to completely view each image perspective; stereoscopic viewing means to view the left image perspective from the camera with one eye of a viewer and to view the right image perspective from the camera with the other eye of a viewer, and synchronization means to synchronize the means for moving the opaque leaf and control the stereoscopic viewing means so that the viewer sees only the left image perspective with the one eye and only the right image perspective with the other eye.

The present invention also provides a method of stereoscopic viewing an object through a two dimensional lens system on a single image path with a camera, comprising the steps of: placing an opaque leaf between the two dimensional lens system and the camera on the single image path; moving the opaque leaf in the single image path between a left position and a right position to provide a left image perspective and a right image perspective of the single image path to the camera, the left image perspective and the right image perspective required for stereoscopic viewing; retaining the opaque leaf stationary in each position for a sufficient time for the camera to completely view each image perspective, and synchronizing alternate left image perspective and right image perspective from the camera with stereoscopic viewing means so that a viewer sees only the left image perspective with one eye and only the right image perspective with the other eye.

BRIEF DESCRIPTION OF DRAWINGS

In drawings which illustrate embodiments of the present invention,

FIG. 1 is a schematic diagram showing a two dimensional single image path system known in the prior art with a lens system and a coupler to a camera, FIG. 2 is a schematic diagram showing the single image path system of FIG. 1 with a switching mechanism according to one embodiment of the present invention placed between the lens system and the camera to provide stereoscopic viewing.

BEST MODE FOR CARRYING OUT THE INVENTION

Figure 3:
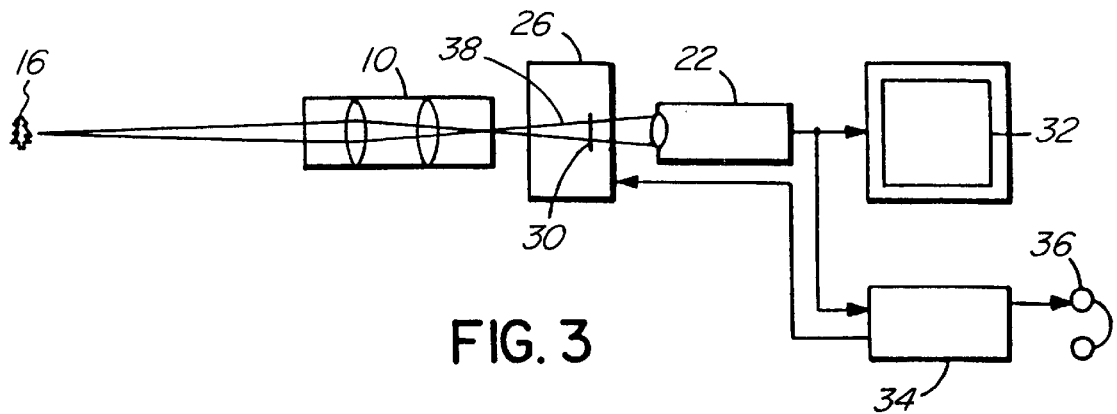
FIG. 3 is a schematic diagram showing the components of the stereoscopic viewing system according to one embodiment of the present invention.

FIG. 1 illustrates a known type of endoscope for two dimensional viewing using a camera. The endoscope 10 has entry lenses 12 and exit lenses 14 with other lens 15 therebetween. Rays from an object 16 pass through the entry pupil and entry lens 12. The rays being limited by the edges of the lens 12, the dimension of the eyepiece (not shown) or entry aperture 18 restrict the angle of the rays that pass through the exit lens 14 and define the exit pupil. A coupler 20 couples the endoscope to the camera 22. The rays are focused by a focusing lens 23 on the light sensitive element 25 of the camera 22. The principal ray 24 is shown at the central axis of the endoscope 10.

FIG. 2 shows the endoscope 10 of FIG. 1 modified for stereoscopic viewing system by placing a switching device 26 between the endoscope 10 and the camera 22. The switching device 26 shifts the perspective of the image path causing the principal ray 24 to change. The principal ray 24 represents the center of the rays passing through the endoscope 10 that are seen by the camera 22. Thus, the camera sees a different perspective view of the object in the single image path. When the switching device 26 is moved to the other side, the principal ray 24 changes.

Referring now to FIG. 3, the lens system 10 is shown diagrammatically with the switching device 26 positioned on the single image path between the lens system 10 and the camera 22. The speed switching device 26 has an opaque leaf 30 positioned at an optimal position to blank off the single image path between the lens system 10 and the camera 22 and provide left and right image perspectives of the object for the single image path. Thus, the image seen by the camera is the same but from different perspectives. The details of the switching device 26 will be disclosed hereafter. The camera 22, which in this drawing is a video camera, provides a signal to a video monitor 32. An electronic synchronizer 34 synchronizes the movement of the high speed switching device 26 with the frame movement of the camera, which in a video camera is the commencement of the vertical retrace, and then provides a signal to a stereoscopic viewing arrangement, in this case illustrated as liquid crystal glasses 36, so that the left and right eye of a viewer are synchronized to view the left and right image perspectives formed by movement of the high speed switch 26 at the location in the single image path where the rays define the exit pupil. Other types of stereoscopic viewing arrangements may be used.

Figure 4:
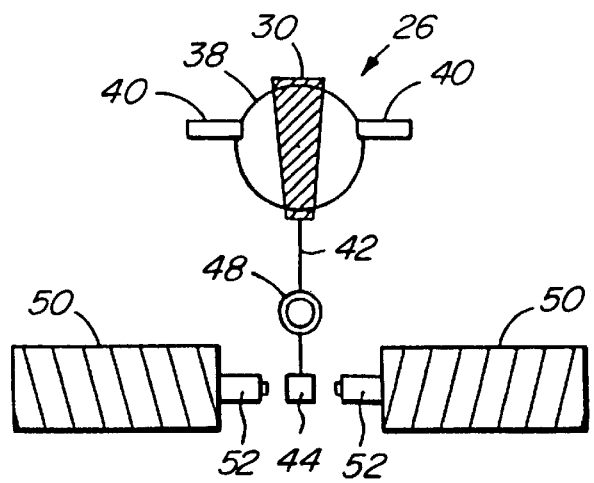
FIG. 4 is a schematic diagram showing the switching device including an opaque leaf for laterally moving in a single image path between a camera and an object.

Details of the high speed switch 26 are illustrated in FIG. 4 wherein an opaque leaf 30 moves laterally in the image path 38 between end stops 40. The opaque leaf 30 blanks off a portion of the complete optical path 40 and when moved from a left position to a right position provides a left image perspective and a right image perspective.

The opaque leaf 30 is supported on the end of an arm 42 which at the other end has a magnetic material armature 44, generally iron. A fulcrum or bearing 48 is positioned on the arm 42. In the optimized case the relative lengths of the arm portions between the opaque leaf 30 and the bearing 48 and between the armature 44 and the bearing 48 are chosen so that it represents the center of the mass forming the opaque leaf 30, arm 42 and armature 44. This provides a balance for the arm 42 to accelerate, stop and be free of motion in the time period between adjacent video or film image frames. In the video embodiment the time period between adjacent frames is approximately 0.5 milliseconds and in the motion picture embodiment this time is the gate mechanism advancement time, generally slightly more than 0.5 milliseconds. The bearing 48 is a low friction bearing allowing the arm 42 to move only in the one plane that is perpendicular to the single image path 38. No other motions are allowed as they cause aberrations or distortion in the image.

The armature 44 is moved by two electromagnets 50 which in one embodiment each having dampers 52 to assist in stopping the armature 44 and hence the opaque leaf 30 quickly and without any vibration.

The opaque leaf 30 is shown being trapezoidal in shape and in a preferred embodiment the side face of the trapezoidal shape extends across the diameter or center line of the single image path 38 when in either the left position or the right position up against end stops 40. The opaque leaf 30 moves in a short space of time and then remains motionless for a relatively long period in both the right position and the left position. For a video camera, this exposure time is 16.7 milliseconds or 33.3 milliseconds at the frame rate. The ratio of 0.5 milliseconds to 16.7 milliseconds defines a 3% duty cycle, or at the frame rate a 1.5% duty cycle. The switching action has to occur in this short period and the opaque leaf 30 has to remain stationary without any movement for the exposure time. Motion of the opaque leaf 30 during the exposure time degrades the image quality.

In the embodiment shown the opaque leaf 30 transverses perpendicularly across one-half of the single image path 38 from end stop 40 to end stop 40 during the frame advancing time period. Many different types of materials may be used for the opaque leaf. The defining parameter is that the leaf material is opaque in the wave length of interest. For example, in the light frequencies the leaf must be opaque to light. The switch functions over a broad range of spectrum from sonic through infrared light, ultraviolet and including high radio frequencies. In fact any frequency that is capable of having a camera produce or reproduce an image. The switching device 26 is placed at a location in the single image path 38 typically at or near to the camera lens. In this way the opaque leaf 30 defines a constraining plane within the image path. In the case of a radio frequency, the camera is an antenna, and in the case of a sonic system, the camera would be a directional microphone, or a horn to receive an ultrasonic beam. In all cases, the opaque leaf 30 divides the image path into a left perspective and a right perspective such that these two perspectives can be viewed by the left and right eyes of a viewer to provide a stereoscopic or three dimensional image.

The left image perspective and the right image perspective are seen by alternating frames of the camera 22 and then as shown in FIG. 3, a signal passes to a video monitor 32 where the left image perspective and the right image perspective are alternately shown from frame to frame. An electronic synchronization circuit 34, shown in FIG. 3, receives a signal from the camera 22 which represents the time between adjacent frames or, in the case of a motion picture, the time that the gate mechanism advances the film from frame to frame, and a signal from the electronic synchronization circuit 34 is passed to the electromagnets 50 of the switching device 22, first the left image perspective and then the right image perspective, to ensure that there is synchronization between the camera 22 and the switching device 26. The electromagnet 50 is activated to move the opaque leaf 30 during the half millisecond that the video or film frame changes and then ensure that the opaque leaf 30 remains motionless during the exposure time of that frame, be it video or film. As shown in FIG. 3, the electronic synchronization circuit 34 also provides a signal to the two optical lenses in liquid crystal shutter glasses 36 similar to the type disclosed in U.S. Pat. No. 4,021,846 to Roese. The different optical lenses change state from transparent to opaque and it is the electronic synchronization circuit 34 which ensures that the left image perspective of the single image path is seen by the left eye with the right optical lens opaque, and the right image perspective of the image path seen by the right eye with the left optical lens opaque. The optical lenses switch from being transparent to opaque at the same speed and in synchronization with the movement of the opaque leaf and thus in synchronization with the frame movement of the camera 10. Thus the alternating image perspectives on the monitor 20 are arranged to be seen by a viewer left eye seeing only the left image perspective frames and right eye only the right image perspective frames.

There are many other mechanisms available to differentiate at a viewers eye between the left image perspective and the right image perspective, and the present invention is not limited to any one type of stereoscopic viewing device.

Figures 5A, 5B, 5C:
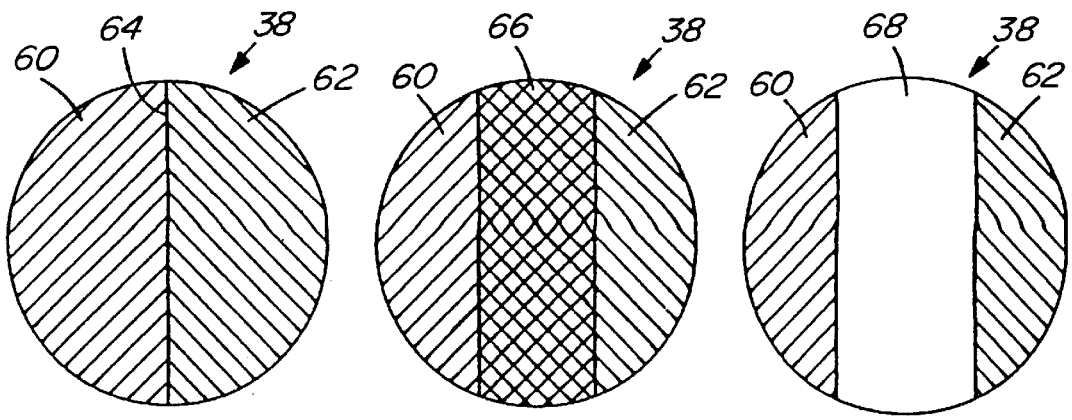
FIGS. 5a, 5b and 5c are schematic views showing circular image paths with different sizes of left and right blocking to provide left and right perspectives.

The location of the end stops 40 shown in FIG. 4 may be relocated if one requires greater or less movement of the opaque leaf 30 across the single image path 38. FIG. 5a illustrates a circular cross-section image path 38 at that location with a left block 60 and a right block 62 to provide a left image perspective and a right image perspective. The trapezoidal shape of the opaque leaf 30 divides the single image path 38 at a vertical diameter 64, thus the two blocks 60,62 have the same cross-sectional areas, each a semi circle. This creates the joining edge of the left block 60 and the right block 62 during the cycling action.

The amount of stereopsis is varied within the image path 38 by changing the movement of the opaque leaf 30 between the end stops 40.

FIG. 5b represents less movement of the opaque leaf, the left block 60 overlaps the right block 62 and has an overlap portion 66. FIG. 5c represents more movement of the opaque leaf and the left block 60 and right block 62 do not even join, leaving a gap 68. A greater stereopsis is obtained with overlap as shown in FIG. 5b but there is less light for viewing. The best light situation occurs with a gap between the blocks 60,62 as shown in FIG. 5c, but there is less stereopsis. A preferred embodiment of optical viewing is the arrangement shown in FIG. 5a which best balances light and stereopsis.

In the embodiment described herein, it has been indicated that the left image perspective is seen by the left eye of a viewer and the right image perspective is seen by the right eye of the viewer. This arrangement may depend partly upon the location of the opaque leaf of the switching device in the single optical path. In certain situations, the perspectives may be physically or electronically varied. The position of perspectives is varied to obtain the desired degree of stereopsis.

Whereas the opaque leaf 30 has been shown as been trapezoidal, in other embodiments this shape may be varied. For instance, the opaque leaf 30 may be such that two separate circular image perspectives are formed spaced apart. Whereas the single image path 38 is shown as being circular, in other embodiments this could be rectangular or almost any shape which is viewed by a camera. In an optical embodiment, the single image path 38 can be scaled larger or smaller as can the switching device 26. Maximum energy transmission is provided for stereoscopic imaging through the single lens system since only one-half the image path 38 is blocked during each cycle as compared to any technique that places energy absorbing devices in series with the active half of a transmission path. The opaque leaf 30 blocks a portion of the image path 38 leaving the remainder of the image path open for an image perspective. No additional devices that absorb energy or distort the properties of the energy source are needed, and there is no change necessary for focusing the right or left image perspectives.

The air gaps that are in position between the armature 44 and the electromagnets 50 provide fast release of the armature 44 from residual magnetic fields stored in the electromagnets 50 for the next cycle. Electronic waveform control on the magnetic fields reduce these residual fields further. The electronic waveform to the electromagnets 50 of the switch mechanism are formed to create high acceleration required during the frame advancing cycle. The waveform then reduces to hold the armature 44 and hence the opaque leaf 30 in place and stationary during the exposure period. In one embodiment, just before the end of the exposure period, the waveform releases and a slight reverse polarization occurs to the electromagnet 50 to overcome residual permanent magnetic effects in the magnet itself. The cycle repeats itself with the opposite electromagnet 50.

Other changes may be made to the embodiments shown herein without departing from the scope of the present invention which is limited only by the following claims.

The embodiments of the present invention in which an exclusive property or privilege is claimed are defined as follows:

1. A method for operating a switching apparatus in a stereoscopic system for producing stereoscopic image paths of variable stereopsis from a single image path, the method comprising:

a) moving a blocking member between first and second locations in said single image path in response to signals received from a synchronizer in communication with an imaging apparatus, to alternately define on opposite sides of said blocking member first and second image path portions of said single image path, said first and second image path portions having first and second spaced apart centroids respectively; and b) adjustably controlling a range of movement of said blocking member to define adjustable sizes of said first and second image path portions and an adjustable distance between said first and second centroids.

2. A method as claimed in claim 1, wherein adjustably controlling includes varying the amount of movement of said blocking member.

3. A method as claimed in claim 2, further including synchronizing alternately defining said first and second image path portions with said imaging apparatus for receiving light from said first and second image path portions respectively.

4. A method as claimed in claim 3, wherein moving a blocking member includes moving an opaque member by alternately activating first and second electromagnets on opposite sides of an armature composed of ferromagnetic material, said armature being connected to a second end portion of an arm having first and second end portions, said first end portion of said arm being connected to said opaque member, said arm having a fulcrum between said opaque member and said armature such that said arm is rotatable, thereby moving said armature between first and second armature locations adjacent to said first and second electromagnets respectively, thereby alternately rotating said arm to move said opaque member between said first and second locations.

5. A method as claimed in claim 4, wherein said arm is rotatable in a plane generally perpendicular to said single image path.

6. A method as claimed in claim 5, wherein synchronizing includes controlling said first and second electromagnets to synchronize said opaque member in said first and second locations with said imaging apparatus for receiving light from said first and second image path portions respectively.

7. A switching apparatus for use in a stereoscopic system for producing stereoscopic image paths of variable stereopsis from a single image path, said apparatus comprising:

a) blocking means for blocking a portion of said single image path;

b) means for moving said blocking means between first and second locations in said single image path in response to signals received from synchronization means in communication with imaging means, to alternately define on opposite sides of said blocking means first and second image path portions of said single image path, said first and second image path portions having first and second spaced apart centroids respectively; and c) means for adjustably controlling a range of movement of said blocking means to define adjustable sizes of said first and second image path portions and an adjustable distance between said first and second centroids.

8. An apparatus as claimed in claim 7, wherein said blocking means includes a movable member, said movable member having an opaque portion disposed in said single image path.

9. An apparatus as claimed in claim 8, wherein said means for controlling includes first and second end stops on opposite sides of said opaque portion, said first and second end stops being adjustable in position to selectively limit a range of movement of said movable member.

10. An apparatus as claimed in claim 9, wherein said movable member is rotatable about an axis generally parallel to said single image path.

11. An apparatus as claimed in claim 10, wherein said means for moving includes at least one electromagnet.

12. An apparatus as claimed in claim 9, wherein said movable member includes:
    a) an arm having first and second end portions, said opaque portion being disposed at said first end portion of said arm;
    b) an armature composed of ferromagnetic material, said armature being connected to said second end portion of said arm; and
    c) a fulcrum on said arm between said opaque portion and said armature, such that said arm is rotatable.

13. An apparatus as claimed in claim 12, wherein said arm is rotatable in a plane generally perpendicular to said single image path.

14. An apparatus as claimed in claim 12, wherein said means for moving includes first and second electromagnets on opposite sides of said armature, operable to move said armature from a first armature location adjacent to said first electromagnet to a second armature location adjacent to said second electromagnet to rotate said arm to move said opaque portion from said first location to said second location.

15. An apparatus as claimed in claim 14, further including:
    a) a first damper on said first electromagnet between said first electromagnet and said armature; and
    b) a second damper on said second electromagnet between said second electromagnet and said armature.

16. An apparatus as claimed in claim 14, further including said synchronization means for controlling said first and second electromagnets to synchronize said opaque portion in said first and second locations with a viewing apparatus for receiving light from said first and second image path portions respectively.

17. An apparatus as claimed in claim 8, wherein said opaque portion includes an opaque leaf.

18. An apparatus as claimed in claim 17, wherein said opaque leaf is trapezoidal in shape.

19. A switching apparatus for use in a stereoscopic system for producing stereoscopic image paths of variable stereopsis from a single image path, said apparatus comprising:
    a) a movable member, having an opaque portion disposed in said single image path;
    b) a switching device cooperating with said movable member, for moving said movable member between first and second positions in response to signals received from a synchronizer in communication with an imaging apparatus, to move said opaque portion between first and second locations in said single image path, to alternately define on opposite sides of said opaque portion first and second image path portions of said single image path, said first and second image path portions having first and second spaced apart centroids respectively; and
    c) a limiter for adjustably controlling a range of movement of said opaque portion to define adjustable sizes of said first and second image path portions and an adjustable distance between said first and second centroids.

20. An apparatus as claimed in claim 19, wherein said limiter includes first and second end stops on opposite sides of said opaque portion, said first and second end stops being adjustable in position to selectively limit a range of movement of said movable member.

21. An apparatus as claimed in claim 20, wherein said movable member is rotatable about an axis generally parallel to said single image path.

22. An apparatus as claimed in claim 21, wherein said switching device includes at least one electromagnet.

23. An apparatus as claimed in claim 20, wherein said movable member includes
    a) an arm having first and second end portions, said opaque portion being disposed at said first end portion of said arm;
    b) an armature composed of ferromagnetic material, said armature being connected to said second end portion of said arm; and
    c) a fulcrum on said arm between said opaque portion and said armature, such that said arm is rotatable.

24. An apparatus as claimed in claim 23, wherein said arm is rotatable in a plane generally perpendicular to said single image path.

25. An apparatus as claimed in claim 24, wherein said opaque portion includes an opaque leaf.

26. An apparatus as claimed in claim 25, wherein said opaque leaf is trapezoidal in shape.

27. An apparatus as claimed in claim 23, wherein said switching device includes first and second electromagnets on opposite sides of said armature, operable to move said armature from a first armature location adjacent to said first electromagnet to a second armature location adjacent to said second electromagnet to rotate said arm to move said opaque portion from said first location to said second location.

28. An apparatus as claimed in claim 27, further including:
    a) a first damper on said first electromagnet between said first electromagnet and said armature; and
    b) a second damper on said second electromagnet between said second electromagnet and said armature.

29. An apparatus as claimed in claim 27, further including said synchronizer for controlling said first and second electromagnets to synchronize said opaque portion in said first and second locations with a viewing apparatus for receiving light from said first and second image path portions respectively.

30. An apparatus as claimed in claim 19, further comprising:
    a) a two dimensional lens system on said single image path; and
    b) a camera;
    c) wherein said opaque portion is positioned between an object viewed by said lens system and said camera.

31. An apparatus as claimed in claim 30, wherein said opaque portion disposed in said single image path is located between said lens system and said camera.

32. An apparatus as claimed in claim 30, wherein said switching device is operable to move said opaque portion from said first location to said second location within 0.5 milliseconds or less.

33. A switching apparatus for use in a stereoscopic system for producing stereoscopic image paths from a single image path, said apparatus comprising:

a) a movable member, having an opaque portion disposed in said single image path; and b) a switching device including at least one electromagnet responsive to signals received from a synchronizer in communication with an imaging apparatus, said electromagnet imposing a force on said movable member, to move said movable member between first and second positions, in which said opaque portion is in first and second locations respectively in said single image path, to alternately define on opposite sides of said opaque portion first and second image path portions of said single image path, said first and second image path portions having first and second spaced apart centroids respectively.

34. An apparatus as claimed in claim 33, wherein said movable member includes:

a) an arm having first and second end portions, said opaque portion being disposed at said first end portion of said arm;

b) an armature composed of ferromagnetic material, said armature being connected to said second end portion of said arm; and c) a fulcrum on said arm between said opaque portion and said armature, such that said arm is rotatable.

35. An apparatus as claimed in claim 34, wherein said arm is rotatable in a plane generally perpendicular to said single image path.

36. An apparatus as claimed in claim 34, wherein said switching device includes first and second electromagnets on opposite sides of said armature, operable to move said armature from a first armature location adjacent to said first electromagnet to a second armature location adjacent to said second electromagnet to rotate said arm to move said opaque portion from said first location to said second location.

37. An apparatus as claimed in claim 36, further including:

a) a first damper on said first electromagnet between said first electromagnet and said armature; and b) a second damper on said second electromagnet between said second electromagnet and said armature.

38. An apparatus as claimed in claim 36, further including said synchronizer for controlling said first and second electromagnets to synchronize said opaque portion in said first and second locations with a viewing apparatus for receiving light from said first and second image path portions respectively.

39. An apparatus as claimed in claim 38, further including a limiter for controlling the movement of said opaque portion to define the sizes of said first and second image path portions and a distance between said first and second centroids.

40. An apparatus as claimed in claim 39, wherein said opaque portion includes an opaque leaf.

41. An apparatus as claimed in claim 40, wherein said opaque leaf is trapezoidal in shape.

42. An apparatus as claimed in claim 34, wherein said opaque portion includes an opaque leaf.

43. An apparatus as claimed in claim 42, wherein said opaque leaf is trapezoidal in shape.

44. A switching apparatus for use in a stereoscopic system for producing stereoscopic image paths from a single image path, said apparatus comprising:

a) a movable member, including
  i) an arm having first and second end portions;
  ii) an opaque portion disposed at said first end portion of said arm and disposed in said single image path;
  iii) a fulcrum on said arm between said opaque portion and said second end portion, such that said arm is rotatable; and b) a switching device cooperating with said movable member, for rotating said movable member alone an arc between first and second positions in response to signals received from a synchronizer in communication with an imaging apparatus, to move said opaque portion between first and second locations in said single image path, to alternately define on opposite sides of said opaque portion first and second image path portions of said single image path, said first and second image path portions having first and second spaced apart centroids respectively.

45. An apparatus as claimed in claim 44, wherein said arm is rotatable in a plane generally perpendicular to said single image path.

46. An apparatus as claimed in claim 44, wherein said opaque portion is trapezoidal in shape.

47. An apparatus as claimed in claim 46, further including:

a) a two dimensional lens system on said single image path; and b) a camera;

c) wherein said opaque portion is positioned between an object viewed by said lens system and said camera.

48. An apparatus as claimed in claim 47, wherein said opaque portion disposed in said single image path is located between said lens system and said camera.

* * * * *